United States Patent [19]

Bianchi et al.

[11] Patent Number: 4,486,429
[45] Date of Patent: Dec. 4, 1984

[54] AMINO DERIVATIVES OF 4-PHENYL 4-OXOBUTEN-2-OIC ACID, PHARMACEUTICAL COMPOSITIONS CONTAINING THEM, AND METHODS FOR PREPARING AND THERAPEUTICALLY USING THEM

[75] Inventors: Mario Bianchi; Fernando Barzaghi, both of Milan, Italy

[73] Assignee: Roussel Uclaf, Romainville, France

[21] Appl. No.: 435,371

[22] Filed: Oct. 20, 1982

[30] Foreign Application Priority Data

Oct. 22, 1981 [IT] Italy ................ 49549 A/81

[51] Int. Cl.³ .................. A01N 43/84; A01N 43/48; C07D 265/30; C07D 295/02; C07D 413/00; C07D 241/02
[52] U.S. Cl. .................. 424/248.5; 424/248.53; 424/248.55; 424/250; 424/300; 424/309; 424/316; 424/319; 544/107; 544/109; 544/110; 544/121; 544/130; 544/141; 544/357; 544/360; 544/372; 544/395; 544/410; 544/129; 546/184; 546/192; 548/579; 560/12; 560/13; 560/19; 560/24; 560/25; 560/34; 562/430; 562/433; 562/439; 260/501.11; 260/501.12
[58] Field of Search .................. 560/12, 19, 34, 24; 260/501.11, 501.12; 562/430, 439, 440, 459; 424/309, 316, 319, 286, 300, 248.5, 248.53; 544/87, 107, 109, 121, 130, 141, 171, 357, 358, 360, 372, 395; 546/192; 548/579

[56] References Cited

U.S. PATENT DOCUMENTS

| 2,532,579 | 12/1950 | Thomas ................ 424/308 |
|---|---|---|
| 2,562,208 | 7/1951 | Papa et al. ................ 424/289 |
| 3,046,301 | 7/1962 | Phillips et al. ................ 560/19 |
| 3,753,997 | 8/1973 | Ash et al. ................ 546/194 |
| 3,763,148 | 10/1973 | Ash et al. ................ 546/326 |
| 3,806,509 | 4/1974 | Lebkuecher et al. ................ 560/19 |
| 3,846,470 | 11/1974 | Raube et al. ................ 260/465 E |
| 3,910,959 | 10/1975 | Vallet ................ 549/445 |
| 3,940,404 | 2/1976 | Ash et al. ................ 546/334 |
| 3,940,487 | 2/1976 | La Croix et al. ................ 424/282 |
| 3,953,463 | 4/1976 | Ash et al. ................ 546/326 |
| 4,017,517 | 4/1977 | Murata et al. ................ 549/436 |
| 4,110,447 | 8/1978 | Gante et al. ................ 424/248.4 |

FOREIGN PATENT DOCUMENTS

| 1282644 | 11/1968 | Fed. Rep. of Germany . |
|---|---|---|
| 2047806 | 4/1972 | Fed. Rep. of Germany ...... 562/459 |
| 2103749 | 8/1972 | Fed. Rep. of Germany . |
| 2501834 | 7/1975 | Fed. Rep. of Germany . |
| 8495M | 8/1973 | France . |
| 2270856 | 12/1975 | France . |
| 55-36434 | 3/1980 | Japan . |
| 591415 | 9/1977 | Switzerland . |
| 588108 | 6/1947 | United Kingdom . |
| 1387733 | 3/1975 | United Kingdom . |

OTHER PUBLICATIONS

Child, R. G., "Fenbufen, A New Anti-Inflammatory Analysis: Synthesis and Structure-Activity Relationships of Analogs, "Journal of Pharm. Sci. (vol. 66, #4, 5/77, pp. 466-476.
European Journal of Medical Chemistry Chimica Therapeutica, vol. 13, No. 3, May-Jun., 1978, H. Orzalesi et al, pp. 259-264.
Chemical Abstracts, vol. 88, No. 5, Jan. 30, 1978, Abstract 37442p.
Journal of the American Chemical Society, vol. 71, No. 4, Apr. 1949, F. K. Kirchner et al, pp. 1210-1213.
Journal of the American Chemical Society, vol. 70, No. 10, Oct. 1948, D. Papa et al, pp. 3356-3360.
European Journal of Medical Chemistry Chimica Therapeutica, vol. 12, Jan.-Feb. 1977, pp. 17-20.
Beilstein, vol. 19, p. 312.
Journal of Pharmaceutical Sciences, vol. 66, No. 4, Apr. 1977, pp. 466-476. Child, Ralph G., et al, "Fenbufen, A New Anti-Inflammatory Analgesic: Synthesis and Structure-Activity Relationships of Analogs".
Journal of Medicinal Chemistry, vol. 15, No. 9, Sep. 1972, pp. 918-922, Markovac, A. et al,-"Antimalarials, 3, 2,6-Bis(aryl)-4-pyridinemethanols with Trifluoromethyl Substituents".
Journal of Organic Chemistry, vol. 35, No. 5, May 1970, pp. 1367-1376, Pettit, George R., et al., "Bufadienolides, 1., Introduction and Base-Catalyzed Condensation of Methyl Ketonds with Glyoxylic Acid".
J.A.C.S., vol. 46, No. 10, Oct. 1924, pp. 2319-2326, Rice, Grace Potter, "The Isomeric Esters of Para-Ethoxy-Benzoylacrylic Acid".
Journal of American Pharmaceutical Association, vol. 37, No. 11, Nov. 1948, pp. 439-449.

Primary Examiner—Natalie Trousof
Assistant Examiner—Bruce D. Gray
Attorney, Agent, or Firm—Stevens, Davis, Miller & Mosher

[57] ABSTRACT

Compounds of the formula I:

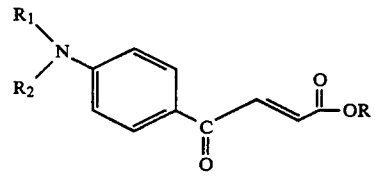

in which R represents a hydrogen atom or an alkyl radical containing from 1 to 8 carbon atoms and $R_1$ and $R_2$, which may be identical or different independently represent a hydrogen atom, an alkyl radical containing from 1 to 4 carbon atoms, a —$CONH_2$ radical, a —$CO_2alk_1$ radical in which $alk_1$ represents an alkyl radical containing from 2 to 8 carbon atoms, or an —$SO_2alk_2$ radical in which $alk_2$ represents an alkyl radical containing from 1 to 8 carbon atoms, or $R_1$ and $R_2$ together with the nitrogen atom form a heterocycle provided that $R_1$ and $R_2$ are not both hydrogen, as well as the alkali metal, alkaline earth metal, ammonium or amine salts of compounds of formula I in which R represents a hydrogen atom. These compounds are useful in treating hyperchlorhydria, gastric or gastroduodenal ulcers, gastritis, hiatal hernias and gastric or gastroduodenal ailments accompanied by gastric hyperacidity. The invention includes pharmaceutical compositions comprising compounds of formula (I) as well as methods of making the compounds.

26 Claims, No Drawings

AMINO DERIVATIVES OF 4-PHENYL 4-OXOBUTEN-2-OIC ACID, PHARMACEUTICAL COMPOSITIONS CONTAINING THEM, AND METHODS FOR PREPARING AND THERAPEUTICALLY USING THEM

The present invention relates to amino derivatives of 4-phenyl 4-oxobuten-2-oic acid, their method of preparation and therapeutic use, as well as compositions containing them.

The present invention is directed to compounds of formula I:

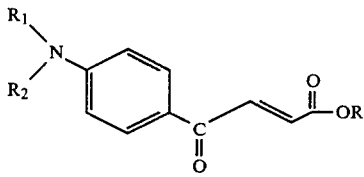

in which R represents a hydrogen atom or an alkyl radical containing from 1 to 8 carbon atoms, and $R_1$ and $R_2$, which may be identical or different, independently represent a hydrogen atom, an alkyl radical containing 1 to 4 carbon atoms, a —$CONH_2$ radical, a —$CO_2alk_1$ radical in which $alk_1$ represents an alkyl redical containing from 2 to 8 carbon atoms, or an —$SO_2alk_2$ radical in which $alk_2$ represents an alkyl radical containing from 1 to 8 carbon atoms, or $R_1$ and $R_2$ together with the nitrogen atom from a heterocycle, provided that $R_1$ and $R_2$ are not both hydrogen as well as the alkali metal, alkaline earth metal, ammonium or amine salts of compounds of formula I in which R represents a hydrogen atom.

The alkali metal or alkaline earth metal salts of the products of formula (I) in which R represents a hydrogen atom may, for instance, be sodium, potassium, lithium or calcium salts.

The amine salts of the products of formula (I) in which R represents a hydrogen atom are the usual amine salts. Among these are monoalkyl amines such as methylamine, ethylamine and propylamine; dialkylamines such as, for instance, dimethylamine, diethylamine and di-n-propylamine; and the trialkylamines such as triethylamine. Piperidine, morpholine, piperazine and pyrrolidine may also be included.

The products of formula (I) may be present in the form of E or Z geometric isomers and these different isomers, of course, fall within the scope of the invention.

When $R_1$ and $R_2$ represents an alkyl radical it is preferably the methyl, ethyl or propyl radical.

When $R_1$ or $R_2$ represents a —$CO_2alk_1$ radical, $alk_1$, preferably represents an ethyl, propyl, isopropyl, butyl, isobutyl or terbutyl radical.

When $R_1$ or $R_2$ represents an —$SO_2alk_2$ radical, $alk_2$ may preferably assume one of the preferred definitions of $alk_1$ identified above, plus a methyl group. When $R_1$ and $R_2$ together with the nitrogen atom form a heterocycle, it is preferably a morpholinyl or N-methyl piperazinyl ring.

When R represents an alkyl radical, it is preferably the methyl, ethyl, propyl, isopropyl or butyl radical.

Particularly preferable are compounds of formula (I) in which R represents a hydrogen atom, those in which $R_1$ represents a hydrogen atom, those in which $R_2$ represents a —$CO_2C_2H_5$ radical, those in which $R_2$ represents a —$CONH_2$ radical, those in which $R_2$ represents an —$SO_2CH_3$ radical and those in which $R_1$ and $R_2$ each represent a methyl radical.

Among the particularly preferred compounds of the invention are the compounds whose preparations are described below in the examples, and in particular, (E) 4-(4-carbethoxyaminophenyl)-4-oxobuten-2-oic acid, as well as its alkaline, alkaline earth, ammonium or amine salts.

The compounds of the invention have useful pharmacological properties and in particular show a substantial anti-ulcer activity in treating ailments of the digestive tract. They also exhibit gastric anti-secretion and cyto-protective activities.

These properties, which are further illustrated in the examples below, justify the use of the compounds of formula I, as well as their pharmaceutically acceptable salts, as drugs.

The object of the invention, therefore, is to provide compounds of formula I as well as the pharmaceutically acceptable alkali metal, alkaline earth metal, ammonium or amine salts of the compounds of formula I in which R represents a hydrogen atom.

The invention more particularly has as its object the compound (E) 4-(4-carbethoxyaminophenyl) 4-oxobuten-2-oic acid, as well as its pharmaceutically acceptable alkali metal, alkaline earth metal, ammonium or amine salts.

The drugs in accordance with the invention are useful in human or animal therapy. The compounds of the invention can be used in treating hyperchlorhydria, gastric or gastroduodenal ulcers, gastritis, hiatal hernias, and gastric or gastroduodenal ailments accompanied by gastric hyperacidity.

The dose, which varies in accordance with the product used and the ailment in question, may range, for instance, between 0.05 and 2 g/day for adults per os.

Still another object of the invention is pharmaceutical composition which contain at least one of the said drugs by way of active principle.

These compositions are produced in such a manner that they can be administered by digestive (oral or rectal) or parenteral route. They may be solid or liquid and be present in the pharmaceutical forms currently used in human or animal medicines, such as, for instance, simple or coated tablets, capsules, granules, suppositories and injectable preparations. The pharmaceutical forms are prepared in accordance with known methods.

The active principle or principles may be incorporated in excipients customarily used in these pharmaceutical compositions such as talc, gum arabic, lactose, starch, magnesium stearate, cocoa butter, aqueous or non-aqueous vehicles, animal or vegetable fats, paraffin derivatives, glycols, various wetting, dispersing or emulsifying agents and preservatives.

Another object of the invention is a method of preparing the compounds of formula I as defined above, which comprises subjecting a compound of formula II:

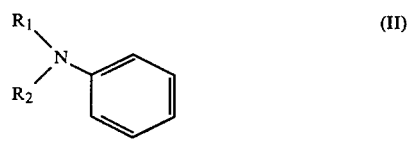

in which R₁ and R₂ have the same meaning as above, to the action of maleic anhydride in order to obtain the corresponding compound of formula I in which R represents a hydrogen atom. This can be subjected, if desired, to the action of a base to form a salt, or to the action of an esterification agent in order to obtain a compound of formula I in which R represents an alkyl radical containing from 1 to 8 carbon atoms.

Another object of the invention is a second process of producing compounds of formula I which comprises subjecting a compound of formula III:

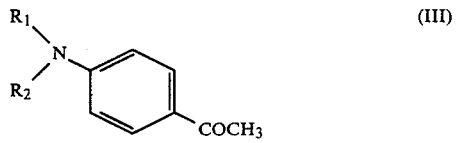

(III)

in which R₁ and R₂ have the same meanings as before, to the action of glyoxylic acid so as to obtain a compound of formula I in which R represents a hydrogen atom.

In a preferred embodiment of the process of the invention, the reaction of the compound of formula II and the maleic anhydride takes place in the presence of catalytic amounts of aluminum chloride, the esterification is effected by means of a functional derivative of an acid, such as an acid chloride or anhydride, or else by reacting the acid itself and an alcohol in the presence of dicyclohexylcarbodiimide or in acid medium, in the presence of hydrochloric, phosphoric or paratoluene sulfonic acid, the alkali metal, alkaline earth metal, ammonium or amine salts of the products of formula I can be prepared by the usual methods, for instance by the reaction of the corresponding bases on the products of formula I in which R represents a hydrogen atom.

In the above process, the glyoxylic acid is preferably formed "in situ" by the action of an acid agent, for instance sulfuric acid, on tartaric acid in the presence of sodium metaperiodate.

The following examples illustrate the invention without, however, limiting it.

EXAMPLE 1

(E) 4-(4-carbethoxyaminophenyl)-4-oxobuten-2-oic acid 8.25 g of ethyl phenylcarbamate and 5.15 g of maleic anhydride were added to a suspension of 25 g of aluminum chloride in 50 cc of dichloroethane. The reaction mixture was stirred for two hours at room temperature, and the complexes were decomposed by carefully adding ice and 50 cc of concentrated hydrochloric acid. The product which separated therefrom was filtered off, washed with water and crystallized in 50% ethanol, after treatment with activated charcoal. The desired product, melting at 210°–212° C., is thereby obtained.

EXAMPLE 2

(E) 4-(ureido phenyl) 4-oxobuten-2-oic acid 6.8 g of phenyl urea and 5.15 g of maleic anhydride were added to a suspension of 25 g of aluminum chloride in 50 cc of dichlorethane, cooled to 0° C. The reaction mixture was stirred for 3½ hours at room temperature, set aside overnight. The compounds were cautiously decomposed by adding ice and 50 cc of concentrated hydrochloric acid. The precipitate formed was filtered and washed with water and then crystallized from 50% ethanol. 7.7 g (66%) of product were obtained, which melted, with decomposition, at 240° C.

EXAMPLE 3

4-(4-methylsulfonyl aminophenyl) 4-oxo-buten-2-oic acid 8.55 g of methylsulfonyl anilide (J. Am. Chem. Soc. 511272-1 1929) and 5.15 g of maleic anhydride were added to a mixture of 25 g of aluminum chloride in 50 cc of dichlorethane cooled to 0° C. After the addition was completed, stirring was continued for 90 minutes at room temperature, whereupon the complexes were decomposed by carefully adding ice and 50 cc of concentrated hydrochloric acid. The solid which was precipitated was filtered off, washed with water and recrystallized from dilute ethanol after treatment with activated charcoal. 8.5 g of the desired product were obtained, melting at 193°–195° C.

EXAMPLE 4

(E) 4-(4-N,N-dimethylamino phenyl) 4-oxobuten-2-oic acid 17.12 g of sodium metaperiodate were added to a solution containing 1.6 cc of concentrated sulfuric acid and 96 cc of water. The mixture was cooled to −5° C. and 12 g of tartaric acid and 25 cc of water were added over a five minute period, with stirring. The stirring was continued for 25 minutes at room temperature and thereupon 13.04 g of p-dimethylamino acetophenone, 12 g of an 0.3 N caustic soda solution, 216 cc of water and 200 cc of ethanol at 95° were added in that order. The reaction mixture was stirred for five hours at room temperature, set aside for two days at room temperature and heated for five minutes at 60° C.

The mixture was cooled and extracted with ether, and the aqueous phase acidified with 2N hydrochloric acid. The product has extracted with chloroform. The organic phase was removed and dried and the solvent evaporated. 11 g of crude product were obtained which were chromatographed over silica, eluting with ether. The expected product was separated and recrystallized from isopropanol. 3.5 g of the desired product melting at 182°–184° C. were obtained.

Pharmaceutical Forms

EXAMPLE 5

Tablets

Tablets were prepared having the following formula:
product of Example 1: 100 mg
excipient q.s. for a finished tablet of: 300 mg
(details of the excipient: lactose, wheat starch, processed starch, rice starch, magnesium stearate, talc).

EXAMPLE 6

Capsules

Capsules of the following formula were prepared:
product of Example 1: 100 mg
excipient q.s. for a finished capsule of: 300 mg
(details of the excipient: talc, magnesium stearate, aerosil).

Pharmacological Study (1) Determination of the anti-gastric secretion activity The technique used is described by H. SHAY et al. in Gastroenterology 5, 43, 1945.

Male rats were used having a weight of about 200 g each (10 animals per lot), and kept without food for 48 hours but enjoying ad libitum 8% glucose solution. After the rats were slightly anesthetized with ether the pylorus of each was ligated. At the end of the operation, the product to be tested was administered intraduodenally in different doses or, for the control animals 0.5% carboxymethyl cellulose solution was administered, whereupon the abdominal incision is sutured.

Three hours later, the animals were sacrificed and their stomachs removed after ligating the esophagus. The gastric juice was removed and centrifuged. The volume of gastric juice obtained was then measured and the total acidity of the gastric juice was determined by titrating a 100 $\mu$'m of gastric juice to a pH of 7 by means of 1/10 N aqueous sodium hydroxide solution.

The percentages of variation in total acidity of the gastric secretions between control and test animals were calculated. The results are set forth in the table which is given below.

(2) Determination of the anti-ulcer activity

Stress Ulcer

The technique consists in inducing stomach ulcers by stress in rats (stress and cold). The technique used is described by E. C. SENAY and R. J. LEVINE, Proc. Soc. Exp. Biol. 124, 1221 (1967).

Female rats weighing about 150 g (5 animals per lot) which have fasted for 48 hours with water ad libitum and glucose solution for 8 hours were used. By an esophageal tube, the animals were administered the test compound, or a solution of 0.5% carboxymethyl cellulose solution for the control animals. Two hours later, the animals were bundled in a jacket of netting. Their paws were bound and the entire unit was placed in a refrigerator at 8° C. for two hours. The rats were released and killed with ether.

Their stomachs were removed, opened along the greater curvature and examined by binocular magnifier. The seriousness of ulceration was clasified from 0 to 3 for each stomach.

For each lot of rats the average intensity of the ulcerations was calculated. The degree of ulceration for control and test animals was determined and the variation expressed in percentage. The results are set forth in the table given below.

(3) Determination of the acute toxicity

The $LD_{50}$ was evaluated after oral administration of the product to mice.

The results are set forth in the following table.

| | RESULTS | | |
|---|---|---|---|
| | | Anti-secretion and anti-ulcer activity (% variation referred to the controls) | |
| Product of Example | $LD_{50}$ mg/kg | Dose mg/kg | Acid Concentration | Ulceration |
| 1 | >1000 | 10 | −55 | −41 |
| 4 | 750 | 10 | −58 | −61 |

What is claimed is:
1. A compound of formula I:

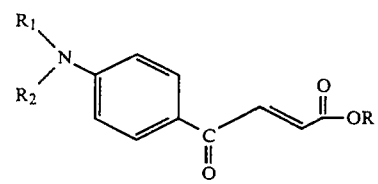

in which R represents a hydrogen atom or an alkyl radical containing from 1 to 8 carbon atoms and $R_1$ and $R_2$ independently represent a hydrogen atom, an alkyl radical containing from 1 to 4 carbon atoms, a —$CONH_2$ radical, —$CO_2alk_1$ radical in which $alk_1$ represents an alkyl radical containing from 2 to 8 carbon atoms, or an —$SO_2alk_2$ radical in which $alk_2$ represents an alkyl radical containing from 1 to 8 carbon atoms or $R_1$ and $R_2$ together with the nitrogen atom form a heterocycle selected from the group consisting of morpholine and N-methyl piperazine, provided that $R_1$ and $R_2$ are not both hydrogen, as well as the pharmaceutically acceptable alkali metal, alkaline earth metal, ammonium or amine salts of the said compounds of formula I when R represents a hydrogen atom.

2. A compound of formula I as defined in claim 1 in which R represents a hydrogen atom, or an alkali metal, alkaline earth metal, ammonium or amine salt thereof.

3. A compound of formula I as defined in claim 1 in which $R_1$ represents a hydrogen atom.

4. A compound of formula I as defined in claim 2 in which $R_1$ represents a hydrogen atom.

5. A compound of formula I as defined in claim 1 in which $R_2$ is selected from the group consisting of a —$CO_2C_2H_5$ radical, a —$CONH_2$ radical and an —$SO_2CH_3$ radical.

6. A compound of formula I s defined in claim 2 in which $R_2$ is selected from the group consisting of a —$CO_2C_2H_5$ radical, a —$CONH_2$ radical and an —$SO_2CH_3$ radical.

7. A compound of formula I as defined in claim 3 in which $R_2$ is selected from a group consisting of a —$CO_2C_2H_5$ radical, a —$CONH_2$ radical and an —$SO_2CH_3$ radical.

8. A compound of formula I as defined in claim 4 in which $R_2$ is selected from the group consisting of a —$CO_2C_2H_5$ radical, a —$CONH_2$ radical and an —$SO_2CH_3$ radical.

9. A compound of formula I as defined in claim 1 in which $R_1$ and $R_2$ each represent a methyl radical.

10. A compound of formula I as defined in claim 2 in which $R_1$ and $R_2$ each represent a methyl radical.

11. (E) 4-(4-carbethoxyaminophenyl)-4-oxobuten-2-oic acid as well as a pharmaceutically acceptable alkali metal, alkaline earth metal, ammonium or amine salt thereof.

12. A pharmaceutical composition for treating hyperchlorhydria, gastric or gastroduodenal ulcers, gastritis, hiatal hernias, or gastric or gastroduodenal ailments accompanied by gastric hyperacidity, comprising a therapeutically effective amount of a compound of formula (I) as defined in claim 1 and a pharmaceutically acceptable excipient.

13. A pharmaceutical composition for treating hyperchlorhydria, gastric or gastroduodenal ulcers, gastritis, hiatal hernias, or gastric or gastroduodenal ailments accompanied by gastric hyperacidity, comprising a therapeutically effective amount of a compound of formula (I) as defined in claim 2 and a pharmaceutically acceptable excipient.

14. A pharmaceutical composition for treating hyperchlorhydria, gastric or gastroduodenal ulcers, gastritis, hiatal hernias, or gastric or gastroduodenal ailments accompanied by gastric hyperacidity, comprising a therapeutically effective amount of a compound of formula (I) as defined in claim 3 and a pharmaceutically acceptable excipient.

15. A pharmaceutical composition for treating hyperchlorhydria, gastric or gastroduodenal ulcers, gastritis, hiatal hernias, or gastric or gastroduodenal ailments accompanied by gastric hyperacidity, comprising a therapeutically effective amount of a compound of formula (I) as defined in claim 5 and a pharmaceutically acceptable excipient.

16. A pharmaceutical composition for treating hyperchlorhydria, gastric or gastroduodenal ulcers, gastritis, hiatal hernias, or gastric or gastroduodenal ailments accompanied by gastric hyperacidity, comprising a therapeutically effective amount of a compound of formula (I) as defined in claim 8 and a pharmaceutically acceptable excipient.

17. A pharmaceutical composition for treating hyperchlorhydria, gastric or gastroduodenal ulcers, gastritis, hiatal hernias, or gastric or gastroduodenal ailments accompanied by gastric hyperacidity, comprising a therapeutically effective amount of a compound as defined in claim 10 and a pharmaceutically acceptable excipient.

18. A method of treating a patient suffering from hyperchlorhydria, gastric or gastroduodenal ulcers, gastritis, hiatal hernias, or gastric or gastroduodenal ailments accompanied by gastric hyperacidity, comprising administering to said patient a therapeutically effective amount of a compound of formula (I) as defined in claim 1.

19. A method of treating a patient suffering from hyperchlorhydria, gastric or gastroduodenal ulcers, gastritis, hiatal hernias, or gastric or gastroduodenal ailments accompanied by gastric hyperacidity, comprising administering to said patient a therapeutically effective amount of a compound of formula (I) as defined in claim 2.

20. A method of treating a patient suffering from hyperchlorhydria, gastric or gastroduodenal ulcers, gastritis, hiatal hernias, or gastric or gastroduodenal ailments accompanied by gastric hyperacidity, comprising administering to said patient a therapeutically effective amount of a compound of formula (I) as defined in claim 3.

21. A method of treating a patient suffering from hyperchlorhydria, gastric or gastroduodenal ulcers, gastritis, hiatal hernias, or gastric or gastroduodenal ailments accompanied by gastric hyperacidity, comprising administering to said patient a therapeutically effective amount of a compound of formula (I) as defined in claim 5.

22. A method of treating a patient suffering from hyperchlorhydria, gastric or gastroduodenal ulcers, gastritis, hiatal hernias, or gastric or gastroduodenal ailments accompanied by gastric hyperacidity, comprising administering to said patient a therapeutically effective amount of a compound of formula (I) as defined in claim 8.

23. A method of treating a patient suffering from hyperchlorhydria, gastric or gastroduodenal ulcers, gastritis, hiatal hernias, or gastric or gastroduodenal ailments accompanied by gastric hyperacidity, comprising administering to said patient a therapeutically effective amount of a compound as defined in claim 10.

24. A method as claimed in claim 18, wherein said compound is administered by digestive route.

25. A method as claimed in claim 18, wherein said compound is administered parenterally.

26. A compound according to claim 1 which is (E) 4-(4-N,N-dimethylamino phenyl) 4-oxobuten-2-oic acid as well as the pharmaceutically acceptable alkali metal, alkaline earth metal, ammonium or amine salts thereof.

* * * * *